(12) United States Patent
Zissu

(10) Patent No.: US 12,106,844 B2
(45) Date of Patent: Oct. 1, 2024

(54) MNEMONIC DEVICE AND A METHOD OF USE THEREOF

(71) Applicant: Diane Zissu, Ossining, NY (US)

(72) Inventor: Diane Zissu, Ossining, NY (US)

( * ) Notice: Subject to any disclaimer, the term of this patent is extended or adjusted under 35 U.S.C. 154(b) by 364 days.

(21) Appl. No.: 17/727,698

(22) Filed: Apr. 22, 2022

(65) Prior Publication Data

US 2022/0344028 A1 Oct. 27, 2022

Related U.S. Application Data

(60) Provisional application No. 63/178,409, filed on Apr. 22, 2021.

(51) Int. Cl.
*G16H 20/70* (2018.01)
(52) U.S. Cl.
CPC .................. *G16H 20/70* (2018.01)
(58) Field of Classification Search
None
See application file for complete search history.

(56) References Cited

U.S. PATENT DOCUMENTS

| 5,863,204 A | * | 1/1999 | Fulton | ........... G09B 1/34 434/167 |
| 2008/0318195 A1 | * | 12/2008 | Murdach | ........... G09B 23/30 434/274 |

FOREIGN PATENT DOCUMENTS

| CN | 202021359752 U | * | 7/2020 | ........... A63H 3/00 |
| DE | 202013003884 U1 | * | 4/2013 | ........... G09B 23/32 |
| WO | WO-2005094959 A1 | * | 10/2005 | ........... A63H 3/16 |
| WO | WO2006134146 | * | 6/2006 | ........... A61K 31/05 |

* cited by examiner

*Primary Examiner* — David J Stoltenberg
(74) *Attorney, Agent, or Firm* — Barry Choobin; Patent 360

(57) ABSTRACT

A mnemonic device/system and a method of use thereof, the mnemonic device includes a base, a set of modules, and a brain head. Each module has a trait inscribed on it and the modules of selected traits are assembled for learning and character building. The mnemonic device provides for pragmatic memory encoding, retention and retrieval, new information to be remembered and encoded by the learner while simultaneously re-coding information previously coded by the teacher. The mnemonic device is based on a scientific sensory system technique providing a unique, and meaningful way, to encode, retain, and retrieve larger pieces of information, especially character word traits in the form of lists like characteristics, steps, and stages, whereby a beneficial use of the system is obtained.

10 Claims, 6 Drawing Sheets

MNEMONIC DEVICE AND A METHOD OF USE THEREOF

CROSS-REFERENCE TO RELATED APPLICATIONS

This application claims priority from the U.S. provisional patent application Ser. No. 63/178,409, filed on Apr. 22, 2021, which is incorporated herein by reference in its entirety.

FIELD OF INVENTION

The present invention relates to a mnemonic device/system and a method for use thereof, and more particularly, the present invention relates to a mnemonic device and a method for building the character of one's personality.

BACKGROUND

Personality refers to a set of characteristics based on how the individual feels, thinks, and behaves. The Personality guides the behavior and habits, how an individual relates to others, make choices, and how one feels about himself—all playing a big part in one's overall mental health and well-being. Mental Health includes emotional, psychological, and social well-being and is important at every stage of life, from childhood and adolescence through adulthood—all these things are affected by the constructs of personality traits, and more specifically the positive traits of one's personality.

Character Strengths are the positive parts of the personality and mental capacity that include elements of behavior, intelligence, and worldview that can impact how one thinks, feel and behave. Studies have found character strengths are significantly correlated with well-being having the biggest impact on one's mental health.

According to the World Health Organization (WHO) (2021), Personality Disorders (PDs) are one of the major problems for the organization of public health systems, defined as a constant pattern of inner experience and behavior that markedly deviates from the social norms and expectations of the culture to which the individual belongs.

Personality Disorders can result in great personal and social costs, including lost productivity, hospitalizations, significant unhappiness, depression, and imprisonment. People with PDs are at risk for alcohol or drug abuse, violent or self-destructive behavior, and even suicide.

But it's the emotional abuse and neglect in children by Parental Personality Disorders that have contributed to the challenge and development of the present disclosure. Both Childhood adverse experiences (CAEs) and personality disorders are prevalent in survivors of one's childhood trauma.

The effect the genes have on one's behavior is entirely dependent on the context of his life as it unfolds day to day, especially during the most fundamental years of neuroplasticity, between the ages of birth to age 3. Based on the genes, no one can say what kind of human being one will turn out to be or what a person will do in life. One thing is known: PDs develop over time. A person does not come down with a Personality Disorder. The disorder arises when something interferes with the development of a healthy personality.

Some attempts at different solutions in regard to PDs have been developed, mainly to help 'manage' crisis behavior. There are a wide variety of types of therapies used by psychologists, clinical psychologists, counseling psychologists, and school psychologists, all bearing the responsibility for evaluating, diagnosing, and treating people for mental, emotional, behavioral, educational, and developmental disorders, many with the band-aid of medication. The treatment therapies for PD prescribed also varies, such as Psychotherapy, Dialectical Behavior Therapy, Cognitive Behavioral Therapy, and Family-Focused Therapy. And to account for the diverse types of personalities, innovations to assess one's Personality such as Personality Type Tests and Personality Games that come to a finish are available. The impact of mental health spending for treatment and services is estimated to have reached 225 billion dollars in 2019 according to a market intelligence report.

Such solutions are all lacking to provide any scientific, technical solution, or relational contribution, to prevent the manifestation of maladaptive personality, a tool to build and develop a healthy personality in a clear, concise, and meaningful way. There is no tangible apparatus and system that has sufficiently addressed the recognition and understanding of the problem—a preventive measure to maximize "well-being"—the character of one's personality in relation to ones, thoughts, feelings, and behaviors.

At this time, there is no known way to prevent personality disorders, and although research on PDs has been limited, no study has been able to show that a person is born with a Personality Disorder. Although the genes are inherited; predispositions to physical appearance and disease, personality is not inherited in any fixed sense.

Thus, a long-term desire is there for a fundamental learning system that is scientifically based and focuses on a more structured mode of memory retention and retrieval in a more clear, concise, and meaningful way.

SUMMARY OF THE INVENTION

The principal object of the present invention is therefore directed to a mnemonic device/system for developing the character of one's personality with the aid of a unique and pragmatic tangible memory aid, that forges a link of association between Psychology and Biology of a person, in a fun and more meaningful, clear, concise way to understand the psychology behind Personality—one's backbone.

The current invention accomplishes the profound challenge of the desired subject matter by maximizing cognitive development to learn, recognize and build the character strengths of personality. Utilizing Semantic Learning with Information Encoding, the scientific memory technique of Metaphor, and a system of Lexical Semantics. All wrapped up in a unique, interesting, and attractive device and method—that is new, unexpected, and unusual, one that will highly motivate and challenge both learner and teacher in a clear, precise, and meaningful way.

In one aspect, disclosed is a mnemonic device based on Biopsychology and the correlation between the human body and brain, and between the biological backbone and psychological backbone, the current invention metaphorically connects the two sciences to learn, recognize, build, and present one's personality. Needed by people of all ages, an inventive contribution lies in the mutuality of the benefits obtained when two or more users and the teacher interact while developing either, both, or all the understanding and importance of one's moral Personality—one's strengths of character.

Disclosed are a device and method that elicits individuals to recognize, change and build the character strengths of their personality, and develop the character strengths of their children, to begin to halt the pernicious cycle of victimization.

In one aspect, disclosed is a method for learning character building and connecting items or ideas to be remember to one visual theme, the method comprising the steps of providing a mnemonic device, the mnemonic device comprising a plurality of modules, the plurality of modules have a plurality of traits, wherein each trait of the plurality of traits is implemented as a word inscribed on an outer surface of the each module, wherein each module is configured to mount over another module of the plurality of modules, wherein each trait of the plurality of traits is unique, a base that has a flat bottom and the each module of the plurality of modules is configured to mount over the base, and a brain head configured to mount over one of the plurality of modules. The method further includes the steps of selecting a first module from the plurality of modules based on the plurality of traits; mounting the first module on a top of the base; selecting a second module from the plurality of modules based on the plurality of traits and the trait of the first module; mounting the second module over the first module; mounting one or more modules from the plurality of modules, one above another, based on the plurality of traits, over the second module; and mounting the brain head over a top module of the one or more modules.

In one implementation, each module of the plurality of modules comprises a ball at its top and a socket at its bottom, wherein the socket is configured to receive the ball to form a ball and socket joint. The top of the base has a socket of the ball and socket joint. The brain head has a ball of the ball and socket joint at its bottom.

In one aspect, disclosed is a mnemonic device for learning character building and connecting items or ideas to be remember to one visual theme, the mnemonic device comprising a plurality of modules, the plurality of modules have a plurality of traits, wherein each trait of the plurality of traits is implemented as a word inscribed on an outer surface of the each module, wherein each module is configured to mount over another module of the plurality of modules, wherein each trait of the plurality of traits is unique; a base that has a flat bottom and the each module of the plurality of modules is configured to mount over the base; and a brain head configured to mount over one of the plurality of modules. The plurality of modules are of a human vertebral bone shape. The each module of the plurality of modules has a plurality of appendages extending from a body of the each module.

BRIEF DESCRIPTION OF THE DRAWINGS

The accompanying figures, which are incorporated herein, form part of the specification and illustrate embodiments of the present invention device and system. Together with the description, the figures further explain the principles of the present invention device and system and to enable a person skilled in the relevant arts to make and use the device and system invention.

DETAILED DESCRIPTION

Figure 1:
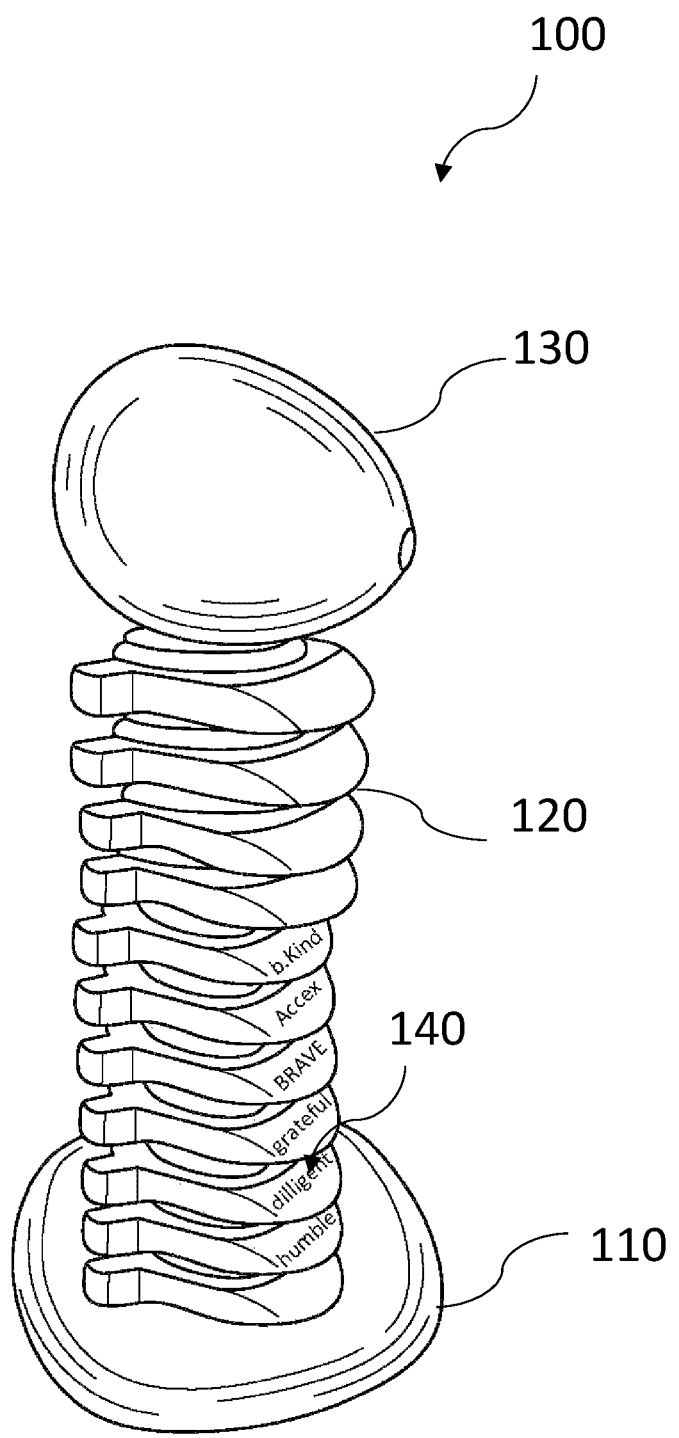
FIG. 1 is a perspective view of the mnemonic device, according to an exemplary embodiment of the present invention.

Subject matter will now be described more fully hereinafter with reference to the accompanying drawings, which form a part hereof, and which show, by way of illustration, specific exemplary embodiments. Subject matter may, however, be embodied in a variety of different forms and, therefore, covered or claimed subject matter is intended to be construed as not being limited to any exemplary embodiments set forth herein; exemplary embodiments are provided merely to be illustrative. Likewise, reasonably broad scope for claimed or covered subject matter is intended. Among other things, for example, the subject matter may be embodied as methods, devices, components, or systems. The following detailed description is, therefore, not intended to be taken in a limiting sense.

The word "exemplary" is used herein to mean "serving as an example, instance, or illustration." Any embodiment described herein as "exemplary" is not necessarily to be construed as preferred or advantageous over other embodiments. Likewise, the term "embodiments of the present invention" does not require that all embodiments of the invention include the discussed feature, advantage, or mode of operation.

The terminology used herein is to describe particular embodiments only and is not intended to be limiting of embodiments of the invention. As used herein, the singular forms "a", "an", and "the" are intended to include the plural forms as well, unless the context indicates otherwise. It will be further understood that the terms "comprise", "comprising,", "includes" and/or "including", when used herein, specify the presence of stated features, integers, steps, operations, elements, and/or components, but do not preclude the presence or addition of one or more other features, integers, steps, operations, elements, components, and/or groups thereof.

The following detailed description includes the best currently contemplated mode or modes of carrying out exemplary embodiments of the invention. The description is not to be taken in a limiting sense but is made merely to illustrate the general principles of the invention since the scope of the invention will be best defined by the allowed claims of any resulting patent.

Disclosed is a mnemonic device that is of configurations of a unique, interesting, and attractive systemic development system with a plethora of buildable modules wherein the user can manually construct the disclosed mnemonic device in a manner that is new, unexpected, and unusual to highly motivate and challenge the user. The ingenuity of the current invention is based on the science of BIOPSYCHOLOGY, forging a link of association with the psychology of the brain and the anatomy of the body's backbone—to build the backbone of one's Personality, more specifically, character strengths to better understand clearly and concisely the psychology behind ones, thoughts, feelings and behavior, and why one behaves the way one does, intending to live a better life, for oneself, children and for all of mankind. Disclosed devices and methods are scientifically based to prevent the manifestation of maladaptive personality, but act as a tool to build and develop a healthy personality in a clear, concise, and meaningful way.

A wealth of evidence, including behavioral studies supported by neuroscientific findings, suggests that the representations of the world are grounded in sensory and physical experiences, and the neural pathways that are used when someone initially experiences those concepts remain encoded in the memory of the brain. It's the 'reuse' of these learned and encoded neural pathways during this time that determines as an adult how one parents the children.

Parental vulnerabilities contribute to insensitive or aggressive reactions, reusing, previous encoded neural pathways, one's experiences, and how they remain habitual in the brain. Research has revealed physiological and neural responses to crying that may predispose some adults to maltreat infants. For example, a crying child conveys evidence about an infant's state and neurological health, a time when consoling safely and lovingly is necessary for healthy brain development, but when crying is inconsolable or judged to be excessive, it can stress parents, disrupt parenting and in many cases, place an infant at risk for abuse and neglect.

The current device and method elicit a parent to learn, recognize, and develop their personality and understand how it controls their thoughts, feelings, and actions, and the information that has been encoded when they were young, can help to understand one's behavior and how this same behavior will be re-coded in the brains of their children. Using the character strengths one can help to protect against and manage and overcome problems, improve relationships, and enhance mental health and well-being. If developed correctly can have a significant impact on the lives, beginning with the lives of the children.

The disclosed device and method intend to draw parallels between how the human body works via its command center, the spinal cord, and backbone, and how the brain works, the psychological backbone of one's personality, the traits as a scientific technique for memory retention and retrieval of new information to be encoded, the object of the current invention is to recode new positive character strengths of both the developing brain of the learner/child and the developed brain of the teacher/parent.

In science communication, metaphors are common throughout many disciplines and help bridge the gap between science and society. Metaphor is recognized as a fundamental cognitive ability that an individual thinks and lives by. Backbone, in the disclosed device and method, is used as a metaphor (and memory device) that dates back to the 1300s and has been a metaphor for character strengths since the mid-19th century.

Metaphors are memory shortcuts and help us to make sense of the unknown through the known. They provide the starting points for understanding something new. Interactive metaphor is one of the central ways of forging a link of association, between old knowledge and radically new knowledge". One's old character traits and one's new Character strengths and a unique and unexpected way to build these traits. And it is exactly the creative and innovative and interactive role of the metaphor of seeing, describing, or interpreting one thing, or experience in terms of another. The current device and method are emblematic of the literal anatomical backbone of vertebrates, specifically, the human backbone, spinal column, having multiple parts; vertebra that when put together make up the apparatus, a backbone, a tangible device one sees, touches, and manually can assemble and build to construct the symbolic structure backbone while simultaneously understanding the relational contribution of what it is representing, the figurative psychological backbone, one's mindset, and the parts, (traits) that makeup of one's personality.

Each part of the psychological backbone, traits, are represented by inscribed word traits to be seen and touched, and learned the meaning of on tactile, 3D parts, during one's everyday comings and goings. The buildable component (metaphor component) represented one's own strengths of character, each component representing a different character trait, one's positive character strengths, one's figurative backbone resembling the vertebra parts are used interactively with the parent/teacher or alone with oneself as the conscious reminder of oneself. A backbone is the part of something that makes it successful and strong.

Since children do not come with manuals, it was the object of the disclosed device to provide the mechanism, a physical parental manual, to be used as an interactive learning device as a clear, concise, and meaningful way to understand the connection between brain and behavior, the mindset. Used for people of all ages during any or all growth stages, and for new parents beginning the development process of their young, the current device, does just that, it's a physical tangible developmental system, the manual, eliciting a learned mindset change from traumatic experiences during childhood to a growth mindset needed in today's culture to build and develop the mind, the brain, of the developing child, specifically the character of one's personality. To begin the Systemic Development and intervention system that can benefit preventive measures addressing and putting a halt to ACE in the children.

The current device and method are age-appropriate for a young child with more rounded diameters of appendages resembling the vertebrae components. Word Traits are inscribed in larger letters more visible for a child and can be a more sophisticated form with smaller print for older users/teachers/learners and not so childlike. Or made of metals or wood for a more masculine design, used by fathers.

The components can be assembled easily one on top of the other can be assembled loosely or with interlocking features. The most inventive contribution of this device and method is while the parent/teacher is interacting with the learner/child by guiding the child to assemble the (vertebrae components) the word traits of character strengths will be learned, by the example of behaviors, and instruction, by both simultaneously providing an unexpected benefit of the systemic development toward a healthy personality, they will also be recognizing one's own developed (previously encoded) personality, simultaneously. The objective is for both learner and teacher to benefit.

The way it works, it would be difficult for a parent or caregiver to teach the word and meaning of kindness (inscribed on a symbolic vertebrae component) to a child, without treating the child with kindness, or recognizing you need to be kind(er). Or teach a child the word and meaning of compassion (inscribed on a symbolic vertebrae component), without caring for the child when distressed, or sad or recognizing the need to have more compassion for a young child. Or the word and meaning of acceptance (inscribed on a symbolic vertebrae component), without accepting a day of frustration just because of the stress of the comings and goings of everyday life, without abuse of a child due to frustration, and recognizing it's one's frustration and not the cause of the child.

These are words, word traits have meaning, and when related to self, one's behavior, the one can learn about self, recognize, and present one's healthy personality according to how the one behaves. For these are the times the current method and device will be used and by who.

Every misbehavior needs to be viewed as the opportunity to recognize the particular character strength that will help manage any situation, by both child and parent, considering the well-being of the child, for as a child reaches their development stage between the ages of 3-5 the word recognition and relational abilities to one's behavior and habits, the encoding of the word traits of character strengths, through the interactive metaphor, will begin to be encoded within the neural pathways for long term retention and retrieval—and become a habit.

The disclosed mnemonic memory device and method when assembled was designed (with artistic license) to mimic the anatomy of the Backbone, (Spinal Column) of Vertebrates. The mnemonic device can mimic other vertebrates for a continual series of relatable and buildable backbones. The Backbone (Mnemonic Device) can have multiple components or modules (metaphor vertebrae) each bearing semblance to human and alternative creative forms of a Vertebrae. When each module is inscribed with word traits of character strengths are put together, one on top of each other, they form the symbolic structure of a Backbone. Using the scientific technique of metaphor meaning one's strength of character, as a memory aid. The first module of the device can sit on a base as the beginning of the sensory learning system to verbally and auditorily, while interacting with the teacher, learn the meaning of and use of the first strength, and continue to assemble additional components (Character strengths), one on top of each other representing different learned sets and stages of personality strengths.

At any level of the stage, during the series of steps, the head (with semblance to a brain) can be placed as a top, designating completion of steps at interval stages of assembled components, representing parts of one's personality with the ongoing goal of building a backbone, from tail to head.

The complex parts (the vertebrae bones) that make up the structure of a spinal column relate metaphorically to the complex parts (character strength traits) that make up one's personality, one's the psychological backbone, providing one with an understanding of the similar structure and a strong sense of self.

Metaphors are a scientific technique used for long-term memory retention and retrieval. The disclosed device is a tangible, 3D model, a hand's-on, user-friendly, interactive tool, a parent can use with their child, with a group, or for oneself. It's a personal character builder and more specifically a character strength builder, consisting of multiple components/modules with different inscribed word traits on each component (module) that when put together bear resemblance to a Backbone, a spinal column of Vertebrates.

The current device elicits one to learn, recognize, and develop as a necessary change while building the personality or character strengths to develop the healthy personality of the child.

The objective benefit to society provided by the present invention embodies multiple inventive features; a sensory device, a memory learning system, a scientific learning technique of metaphor, the interactivity between the learner-centered and the teacher-centered user, manual, hands-on-user-friendly, and fun manual assembling learning/building system, providing a solution to an otherwise nonmeaningful way to solutions regarding the prevention and change of PDs.

The objective benefit to society provided by the present invention is to combat the current state of mental health and personality disorders facing mankind, as a first step, a preventive measure to maximize something a person choose to call "well-being" or utility or "happiness" or flourishing—a healthy personality.

Disclosed are a device and method that allows persons to learn, recognize, build and present their personalities. People of all ages can use the disclosed metaphor device to recognize and present their personalities. For children, the disclosed apparatus can be used to interactively teach good character and allows the children to learn, recognize, and present their personalities. Children can use the disclosed device to actually learn, recognize, and build one's own set of character traits, visually, tactilely, physically, cognitively and begin to embed (encode) the meaning of the words that consist of the vocabulary of character and personality traits, a correlation or analogy as to the meaning of character or personal traits and the understanding and belief-system one has of self.

Referring to FIG. 1 which discloses an exemplary embodiment of a mnemonic device 100 for learning, recognizing, and character building. The device can include a base 110, module 120 that resembles vertebral bones, and a brain-head 130. The modules can be in the form of human vertebral bones and can be assembled one above another to erect the vertebral bone-shaped device 100 as shown in FIG. 1. The mnemonic device 100 resembles the shape of the Vertebral Column or Backbone, having a base 110 at the bottom and the brain head 130 at the top. The base can be any structure of any shape, color, or design that can stabilize the mnemonic device on a support structure, such as a table. The base can have some weight to prevent the mnemonic device from falling under its weight.

The modules 120 resembling vertebral bones can include suitable fastening means to mount the modules to the base and on another module. In one implementation, the fastening mechanism can have two interlocking members, such as a ball and socket joint, wherein one member of the two interlocking members can be provided on the top surface of the base, each module can have the one member on its bottom and another member of the two interlocking members on its top. The brain head 130 can have one member of the two interlocking members on its bottom. The module can be placed over the base or another module and lightly pressed down to interlock the ball onto the socket. Optionally each assembled module in the mnemonic device may not separate unless some release pressure is applied to separate.

To erect a mnemonic device, representing a Backbone, the metaphor for character strengths of one's personality, a base can first be placed on a flat surface. Thereafter, the modules can be mounted one above another (and maybe) secured by the fastening mechanism on the base, and finally, the brain head can be mounted to the topmost module. The building of the mnemonic device starts from the bottom and ends at the top.

Figure 2:
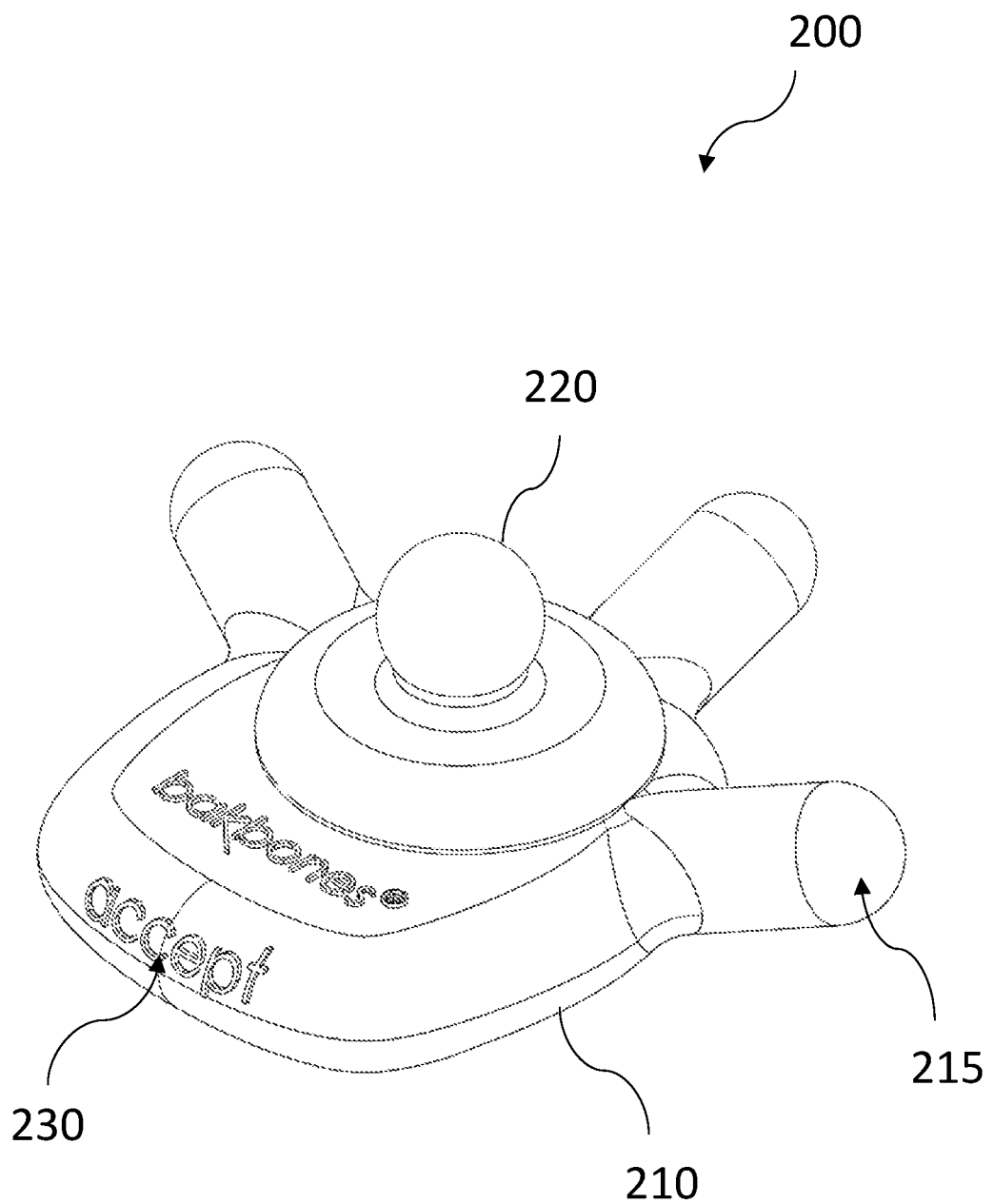
FIG. 2 is a top and side perspective view of a module of the mnemonic device, according to an exemplary embodiment of the present invention.
Figure 3:
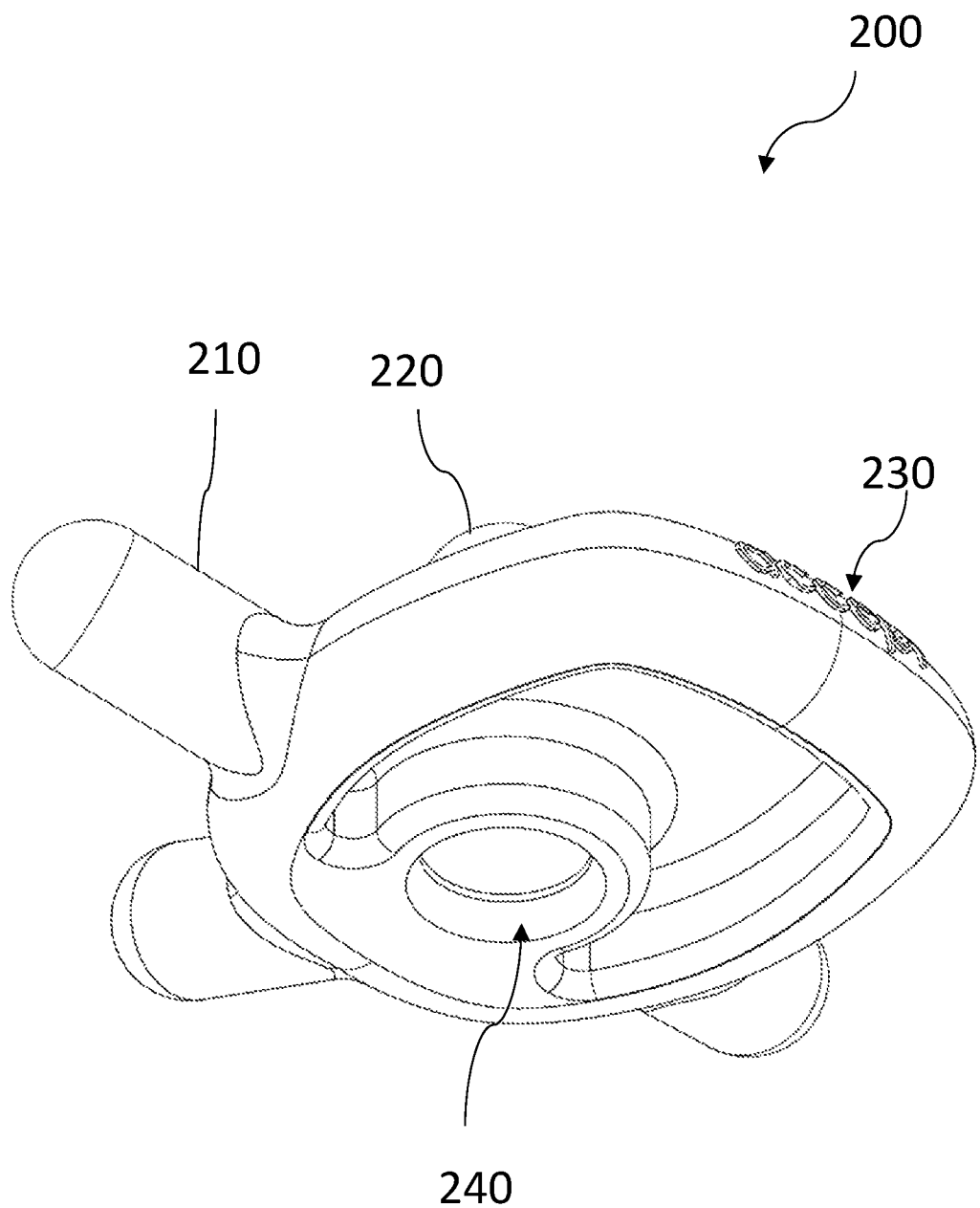
FIG. 3 is a bottom and side perspective view of the module, according to an exemplary embodiment of the present invention.
Figure 4:
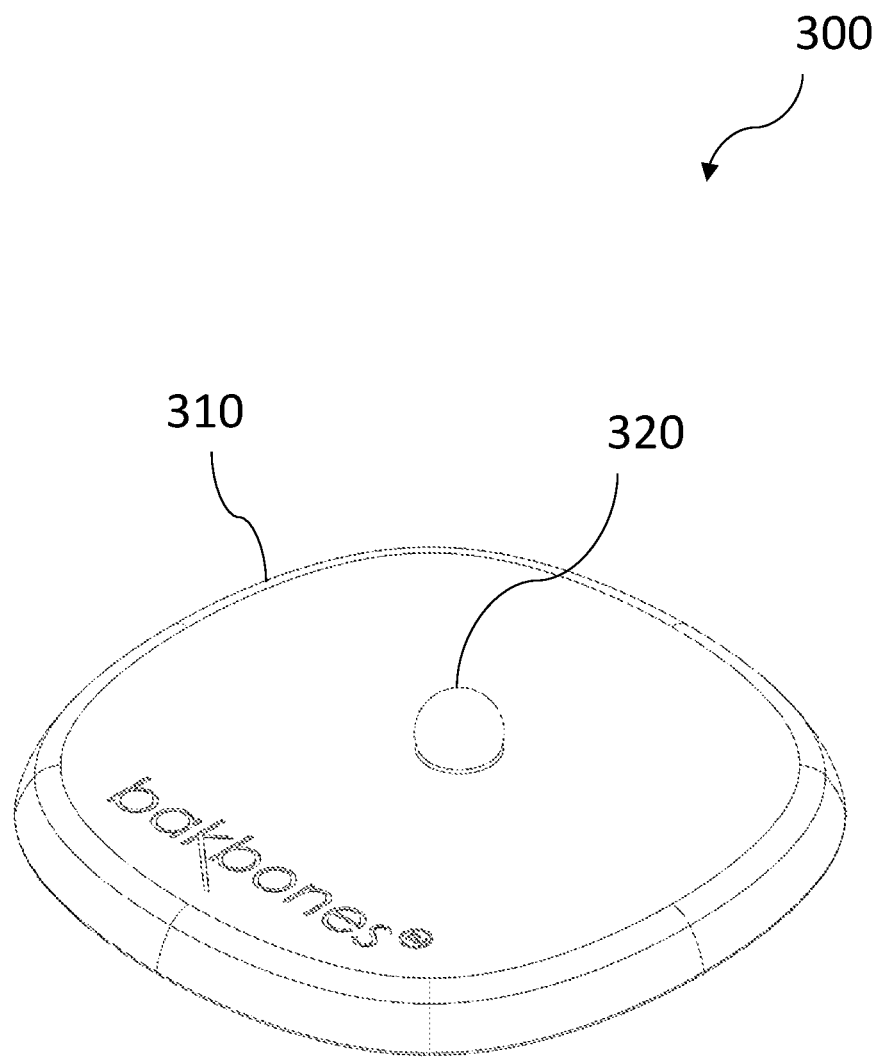
FIG. 4 is a top and side perspective view of the base of the mnemonic device, according to an exemplary embodiment of the present invention.
Figure 5:
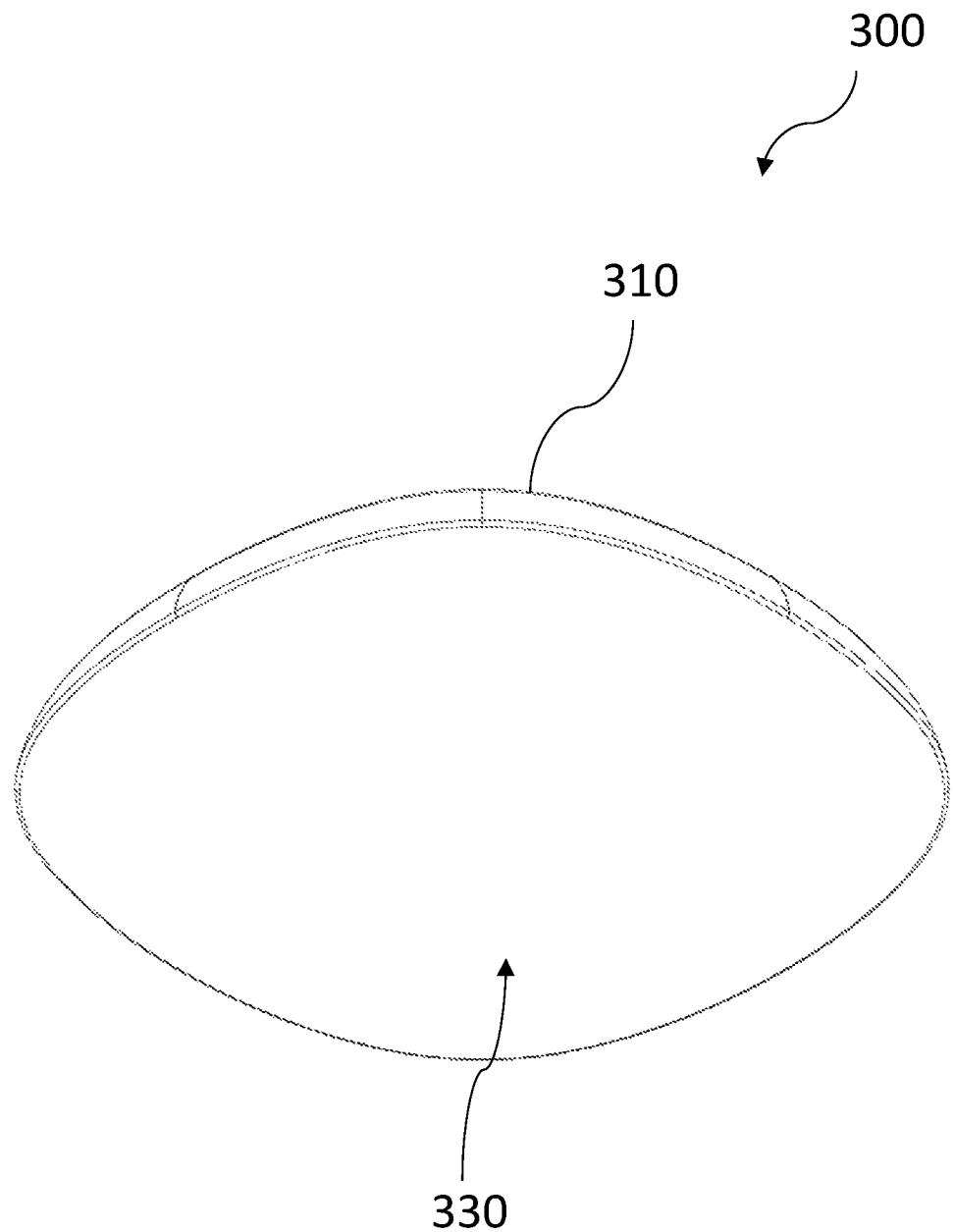
FIG. 5 is a bottom and side perspective view of the base, according to an exemplary embodiment of the present invention.
Figure 6:
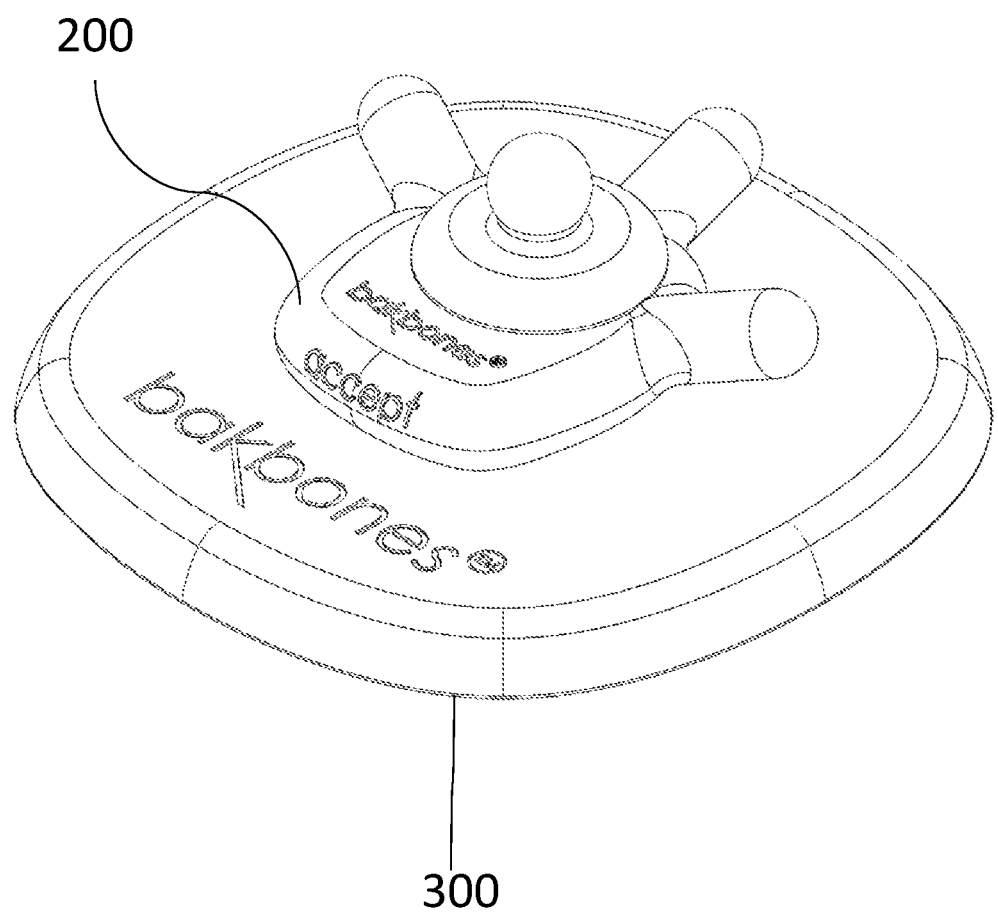
FIG. 6 shows a module of the mnemonic device mounted on the base, according to an exemplary embodiment of the present invention.

Relating to how each vertebra of the human body is connected from the bottom of the human spine up to the base of the head. Each module in the mnemonic device. The number of growth stages or steps or the modules can be varied. For example, for children, the number of modules or growth stages can be less than that for adults. In one case, the mnemonic device can have 24 vertebrae components/modules similar to the number of bones in a human vertebra. Each module can be associated with a unique emotion, feeling, characteristic, habit, mood, or trait. The emotion, feeling, characteristic, habit, mood, or trait are collectively referred to herein as a "trait". The trait can be expressed using dictionary words or vocabulary. The traits as words can be imprinted, inscribed, engraved, applied, or molded on or in each module. FIG. 1 shows the trait 140 inscribed on the module 120. Suitable examples of the character strengths include characteristics of Acceptance, Bravery, Compassion, Diligence, and Empathy. Suitable examples of emotions include Happy, joy, interest, hope, and awe. Suitable examples of traits characteristics include justice, equality, unity, success, consideration, teamwork, perseverance, and dedication. The fastening mechanism may or may not allow the assembled modules to be able to tilt back and forth, turn front to back, side to side, and twist or spin 360 degrees while interlocked, promoting an interactive hand-eye coordination and tactile experience retaining interest. Each growth stage in the mnemonic device can be ordered from bottom to top as the human vertebral column. Referring to FIGS. 2 and 3 which show module 200 that has projections 215 (appendages) protruding from a body 210 as part of the design similar to human vertebrae or vertebrates and differences in size to simulate the lumbar, thoracic, and cervical bones of the human spine, and when turned either clockwise or counterclockwise, said projections (arms of the design) can align or not with the vertebrae below. For each growth stage, a set of modules and thus the traits can be provided. The module 200 has a ball 220 of the ball and socket joint as the fastening mechanism. A trait 230 can also be seen inscribed on the front of the module 200. bottom of the module 200 has a socket 240 of the ball and socket joint. FIGS. 4 and 5 show an exemplary embodiment of the base 300 that has a body 310 and a ball 320 of the ball and socket joint. The bottom 330 of the base 300 is flat. FIG. 6 shows the module 200 mounted on the base 300.

Children can be taught the meaning of each trait and the children can pick the desired module from the set of modules for each growth stage and erect the mnemonic device. The brain-head can resemble the brain and could be provided in assorted colors. This allows both an understanding of the anatomy of a backbone, and the metaphoric meaning of a backbone in relation to oneself and or character. AS THE METAPHOR; "ONE HAS THEIR HEAD ON STRAIGHT" The interactive challenge aspect is to keep the backbone uniform while keeping the user's attention working the 'ball and socket' mechanism along with the movable directions of the vertebrae parts.

The purpose of movement as opposed to just a permanent locking mechanism can be to replicate the curvature of the human spine. An additional aspect can be to have tactile fidget, where the user can manipulate the multiple units to create their curvature or not of vertebrae as they are constructed at different levels of cognitive learning and accomplishment; depending on how many vertebrae are added at a time, by holding the number of the vertebrae, separate from the base, similar to a 'SLINKY' or while interlocked on the base as a 3D Model, the user can get psychologically motivated.

The Brain-head represents the command center for the body, and the spinal cord is the pathway for messages sent by the brain to the body and from the body to the brain. Not only do they control body's movements, but also the senses, thoughts, and memories. The nervous system controls behavior, from the tailbone to the head (brain).

The Brain-Head is placed on top of any number of vertebrae, finishing off a short count or topping the maximum vertebra constructed, and can tilt upwards or downwards, side to side, or rotate 360% facing any direction the user desires to emphasize an expression of accomplishment; as in head upward facing to jester a positive disposition or accomplishment, one's positive view of their character, of the characteristic traits that make up one or more of a series of steps, while manually assembling the structure and considered not complete, as the kit as the backbone set has at least 12-character traits, to begin with, and the user can purchase add additional learned traits.

While the foregoing (just mentioned or stated, aforementioned) written description of the invention enables one of ordinary skill to make and use what is considered presently to be the best mode thereof, those of ordinary skill will understand and appreciate the existence of variations, combinations, and equivalents of the specific embodiment, method system, and examples herein. The invention should therefore not be limited by the above-described embodiment, method system, and examples, but by all embodiments and methods systems within the scope and spirit of the invention as claimed.

What is claimed is:

1. A method for learning character building and connecting items or ideas to be remember to one visual theme, the method comprising the steps of:
   providing a mnemonic device, the mnemonic device comprising:
      a plurality of modules, the plurality of modules have a plurality of traits, wherein each trait of the plurality of traits is implemented as a word inscribed on an outer surface of the each module, wherein each module is configured to mount over another module of the plurality of modules, wherein each trait of the plurality of traits is unique,
      a base that has a flat bottom and the each module of the plurality of modules is configured to mount over the base, and
      a brain head configured to mount over one of the plurality of modules;
   selecting a first module from the plurality of modules based on the plurality of traits;
   mounting the first module on a top of the base;
   selecting a second module from the plurality of modules based on the plurality of traits and the trait of the first module;
   mounting the second module over the first module;
   mounting one or more modules from the plurality of modules, one above another, based on the plurality of traits, over the second module, to erect a backbone of a human vertebrae shape; and
   mounting the brain head over a top module of the one or more modules.

2. The method according to claim 1, wherein each module of the plurality of modules comprises a ball at its top and a socket at its bottom, wherein the socket is configured to receive the ball to form a ball and socket joint.

3. The method according to claim 2, wherein the top of the base has a socket of the ball and socket joint.

4. The method according to claim 3, wherein the brain head has a ball of the ball and socket joint at its bottom.

5. A mnemonic and therapeutic system for learning character building, connecting items or ideas to be remember to one visual theme, and for use by therapists and psychologists for psychological therapy, the mnemonic and therapeutic system comprising:
   a plurality of modules, the plurality of modules have a plurality of traits, wherein each trait of the plurality of traits is implemented as a word inscribed on an outer surface of the each module, wherein each module is configured to mount over another module of the plurality of modules, wherein each trait of the plurality of traits is unique;
a base that has a flat bottom and the each module of the plurality of modules is configured to mount over the base; and
a brain head configured to mount over one of the plurality of modules.

6. The mnemonic and therapeutic system according to claim 5, wherein plurality of modules are of a human vertebral bone shape, and the mnemonic and therapeutic system is of a human vertebra shape.

7. The mnemonic and therapeutic system according to claim 6, wherein each module of the plurality of modules has a plurality of appendages extending from a body of the each module.

8. A backbone system used for learning character building, connecting items or ideas to be remember to one visual theme, and for use by therapists and psychologists for psychological therapy, and the backbone system comprising:
a plurality of modules, the plurality of modules has a plurality of traits, wherein each trait of the plurality of traits is implemented as a word inscribed on an outer surface of the each module, wherein each trait of the plurality of traits is unique,
wherein the backbone system signifies an overall character of a person.

9. The backbone system of claim 8, wherein the plurality of modules are put together to form a shape of a human backbone or spinal column.

10. The method according to claim 1, wherein the selection of the first module, the second module, and the one or more modules is done by a child/learner based on a description of the plurality of traits by a parent/teacher respectively.

* * * * *